United States Patent
Varadaraj et al.

Patent Number: 5,585,516
Date of Patent: Dec. 17, 1996

[54] TWO TAIL-TWO HEAD AND TWO TAIL-ONE HEAD SURFACTANTS

[75] Inventors: Ramesh Varadaraj, Flemington; Stephen Zushma, Clinton, both of N.J.

[73] Assignee: Exxon Research and Engineering Company, Florham Park, N.J.

[21] Appl. No.: 402,071

[22] Filed: Mar. 10, 1995

[51] Int. Cl.⁶ .......................... C07C 309/07; C07C 43/11
[52] U.S. Cl. .................. 562/42; 562/45; 562/77; 568/609
[58] Field of Search .................. 562/42, 45, 77; 568/609

[56] References Cited

PUBLICATIONS

Corbin, et al., J. Org. Chem. 53(22), 5384–6 1988.

*Primary Examiner*—Joseph Conrad
*Attorney, Agent, or Firm*—Joseph J. Dvorak

[57] ABSTRACT

The present invention relates to novel two tail-two head and two tail-one head surfactants. In one embodiment, the present invention comprises a novel composition of matter having the general formula:

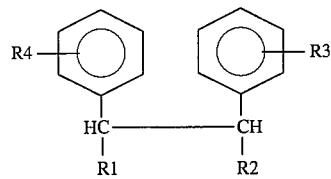

wherein R1 and R2 may be the same or different and are selected from liner or branched hydrocarbon chains with carbon numbers 8 and 22;
R3 is H, $SO^-_y M^+$, or $-O(CH2CH2O)_n X$;
R4 is $SO^-_y M^+$, or $-O(CH2CH2O)_n X$;
M is H, Li, Na, K, Rb or Cs;
n is an integer from 2 to 50;
y is 3 or 4; and,
X is H or $SO^-_y M^-$.
Preferably, in the above composition when R3 is other than H, R3=R4.

9 Claims, 1 Drawing Sheet

TWO TAIL-TWO HEAD AND TWO TAIL-ONE HEAD SURFACTANTS

FIELD OF THE INVENTION

The present invention relates to novel surfactants with two hydrocarbon chains and one or two hydrophilic groups.

BACKGROUND OF THE INVENTION

Surfactants are amphiphilic molecules that manifest their properties at interfaces, e.g., the air-liquid, liquid-liquid and solid-liquid interfaces. They can be either water or oil soluble and are of considerable commercial importance because of their applications in petrochemical, pharmaceutical and soap industries. Generally, a surfactant molecule is characterized by the presence of a hydrophobic group, e.g., a long chain hydrocarbon (tail) attached to a hydrophilic group (head). The hydrophilic head group can be an anionic, cationic or non-ionic moiety and accordingly, surfactants are classified as anionic, cationic or non-ionic surfactants. The vast majority of synthetic surfactants known in the art are molecules with one long hydrocarbon chain attached to one head group. Variations reported in the art include branched hydrocarbon chains and fluorocarbon chains as tails. Surfactant molecules with two hydrocarbon chains attached to one or two head groups are relatively rare.

SUMMARY OF THE INVENTION

Broadly stated, the present invention relates to novel two tail-two head and two tail-one head surfactants. In one embodiment, the present invention comprises a novel composition of matter having the general formula:

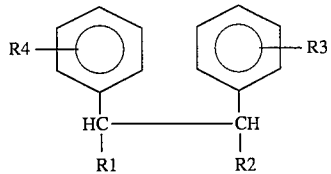

wherein R1 and R2 may be the same or different and are selected from liner or branched hydrocarbon chains with carbon numbers 8 to 22;
R3 is H, $SO_y^-M^+$, or $-O(CH2CH2O)_nX$;
R4 is $SO_y^-M^+$, or $-O(CH2CH2O)_nX$;
M is H, Li, Na, K, Rb or Cs;
n is an integer from 2 to 50;
y is 3 or 4; and,
X is H or $SO_y^-M^+$.

Preferably, in the above composition when R3 is other than H, R3=R4.

BRIEF DESCRIPTION OF THE DRAWING

The accompanying Figure is a plot showing the surface tension profile (surface tension vs. ln (concentration) of two isomeric compounds of the invention.

DETAILED DESCRIPTION

Figure 1:
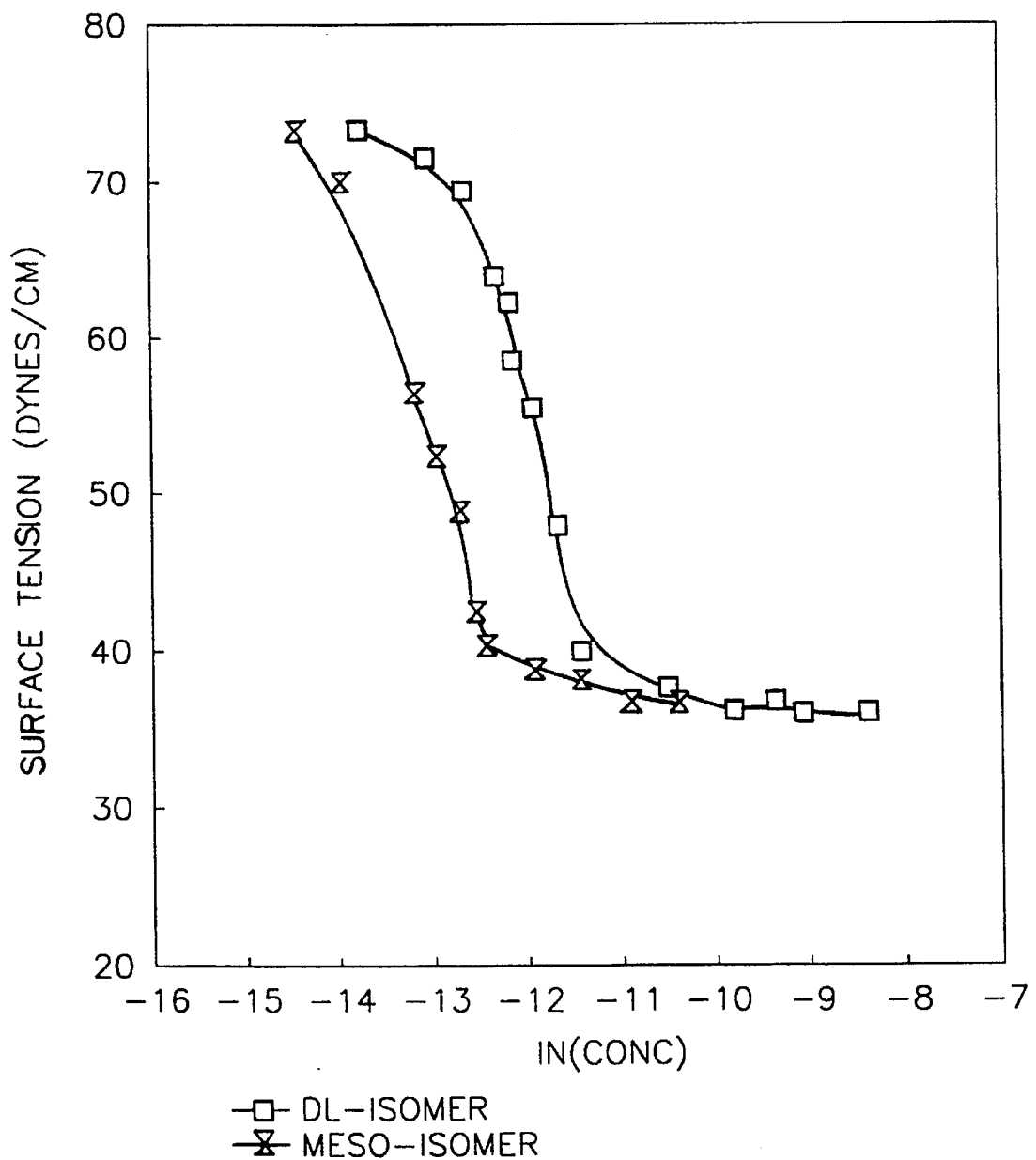

The novel compounds of the present invention are prepared by the general procedure outlined below.

Alkylation Step

In the first step, an alkyl lithium compound, R1Li, wherein R1 is selected from linear or branched hydrocarbon chains with carbon numbers 8 to 22, is contacted with stilbene, a dihydroxyl stilbene, preferrably 4,4'-dihydroxy stilbene or a monohydroxy stilbene such as 4-hydroxy stilbene to provide a lithium containing intermediate. Typically the contacting will be conducted in an inert solvent. Generally, a molar excess of the alkyl lithium compound will be used. Preferred solvents include ethers such as diethyl ether and tetra-hydrofuran.

For convenience, the alkyl lithium compound, R1Li, can be prepared in an ether solvent by contacting excess Li and an alkyl bromide at temperatures in the range of $-30°$ C. to about 20° C. Optionally, but preferably an equimolar amount of tetramethyl ethylene diamine in an ether solvent is then added to the R1Li at a temperature of $-40°$ C. to $-50°$ C. The stilbene compound slurried in an ether solvent is then slowly added to the reaction mixture at $-40°$ C. to $-50°$ C. After the addition of the stilbene compound is complete, the reaction mixture is allowed to slowly rise to 25° C. and stirred at this temperature for 18 to 20 hours to yield the lithium containing intermediate.

The lithium containing intermediate is subsequently contacted with R2Br wherein R2 is selected from linear or branched hydrocarbon chains with carbon numbers 8 to 22 to provide the corresponding dialkylated derivative. The second alkylation step is carried out by adding R2Br in an ether solvent to the lithium containing intermediate at 25° C. and stirring for 2 to 3 hours.

The dialkylation procedure described produces isomeric products: the dl-diastereomeric pair and the meso isomer. When isomer separation is desired fractional crystallization or HPLC techniques can be advantageously employed to isolate the dl pair and meso isomer. Optionally, the mixture of isomers can be subjected to further functionalization without separation.

Functionalization Step (a) Sulfonation

The dialkyl derivative of stilbene can be subjected to sulfonation by standard techniques shown in the art. For example, the dialkylated derivative of stilbene may be contacted with chlorosulfonic acid at the appropriate molar equivalent, e.g., 1 mole stilbene derivative per 2 or more moles chlorosulfonic acid, in methylene chloride at 0° C. The sulfonic acid derivative is subsequently neutralized with the desired base to produce the sulfonate surfactant of the invention.

(b) Sulfation

The dialkyl derivative of the hydroxy or dihydroxyl stilbene can be subjected to sulfation by techniques generally known in the art. For example, the dialkylated hydroxy or dihydroxy derivative is dissolved in pyridine, cooled to 0° C., and then reacted with sufficient chlorosulfonic acid. The amount of chlorosulfonic acid used will, of course, depend upon whether the mono or dihydroxy derivative is being subjected to sulfation. Then the desired base, sodium hydroxide, potassium hydroxide or the like, is added to form the salt of the sulfate.

(c) Ethoxylaytion

Both the dialkylated hydroxy and dihydroxy derivatives of stilbene can be ethoxylated with ethylene oxide and conventional ethoxylation catalysts like sodium or potassium hydroxide. Typically, the ethoxylation reaction is carried out between 0° C. to 5°C. in solvents like tetrahydrofuran and dioxane.

To produce the ethoxysulfate, the ethoxylated product is sulfated by following the sulfation procedure described earlier.

Product isolation and purification is generally accomplished by vacuum distillation followed by fractional crystallization from suitable solvents such as acetone and acetone-methanol mixtures and the like.

EXAMPLE 1

This example details the synthesis, including the isolation of the isomers of a two tail-two head surfactant of the invention wherein $R1=R2=n-C_{10}H_{22}$, $R3=R4=SO_{-y}$ $M^+$, $M=Na$ and $y=3$.

Preparation of Dialkylated Derivative of Trans-Stilbene (Alkyl Group=Decane)

1-bromodecane, 149.4 gm (0.66 mole) in 100 mL of diethyl ether was rapidly added to a suspension of lithium, 9.0 gm (1.26 gm-atom), in 300 mL of diethyl ether cooled at −20° C. After addition, the mixture was stirred for 18 hours while the temperature rose to 25° C. The mixture was then cooled to −40° C. and tetramethyl ethylene diamine, 69.6 gm (0.6 mole), in 100 mL of diethyl ether was added, followed by trans-stilbene, 54 gm (0.3 mole) slurried in 300 ml of diethyl ether. The mixture was stirred for 18 hours at room temperature. 1-bromodecane, 66.6 gm (0.3 mole), in 200 ml of diethyl ether was added next and the mixture poured into water. The ether layer was washed successively with 10% hydrochloric acid, 10% sodium bicarbonate, saturated sodium chloride and dried over anhydrous magnesium sulfate. Ether was removed under vacuum to give crude product. The residue was distilled under reduced pressure (0.1 mm) to yield 28 gms. of the dialkylated derivative (bp=210° C./0.1 mm).

Isomer Separation and Characterization

The meso isomer was separated from the mixture by recrystallization from acetone at −10° C. Single crystal x-ray analysis confirmed the isomer structure. Elemental analysis: found % C 88.23, % H11.64, calcd % C88.25, % H11.76; mp=57° C.

The dl isomeric pair was isolated from the residue by recrystallization from acetone using an isopropyl alcohol/dry ice bath. Elemental analysis: found % C88.41, % H11.63, calcd, % C88.25, % H11.76. The product was a liquid at room temperature.

Proton NMR was used to characterize the isolated isomers. For the meso isomer the chemical shifts of the methine and aromatic protons are at 2.65 and 7.25δ whereas the corresponding shifts for the dl enantiomeric pair occur at 2.78 and 7.08δ. The coupling constant, J(400 MHz proton carbon-13 satellite spectrum with all methylene protons decoupled from the methine protons) was determined to be 10 Hz for the meso isomer. This indicates that the methine protons are trans as the predominant conformer in deuteriochloroform solution.

Sulfonaton of Dialkylated Derivative

Each isomer was sulfonated separately to obtain the pure sulfonated product according to the following procedure.

Chlorosulfonic acid, 4.43 gms (0.04 mole), in 100 mL methylene chloride was added dropwise into a solution of 8.00 gms (0,017 mole) of the dialkylated derivative, in 100 mL of methylene chloride at 0° C. and the mixture warmed to 25° C. and stirred. After 8 hours of reaction methylene chloride was evaporated off and the solution neutralized with sodium methoxide to pH 8 in methanolic medium. Methanol was then evaporated and a 50/50 ethanol/water solution was added to the product and cooled to −10° C. to crystallize the sulfonated product.

The isomeric purity of the disulfonate product was demonostrated by complete chromatographic separation by HPLC using a Varian Instrument LC 5000, with UV-50 detection. With the following conditions, Whatman Partisil 5ODS-3 column, 80:20 acetonitrile/Waters PIC, and a reagent at a flow rate of 1 mL/min., the retention times for the meso disulfonate isomer and dl disulfonated isomeric pair were 3.5 and 9.3 minutes respectively. The followng $C^{13}$ NMR data and elemental analysis were obtained for the disulfonated isomers:

Disulfonated dl-enantiomeric Pair:

$C^{13}$NMR (DMSO):δ145.38 (2C), 143.8(2C), 127.74 (2C), 124.94(2C), 50.02 (2C), 32.70, 31.26, 28.95, 28.61, 26.88 (16C), 22.04(2C), 13.88(2C).

Elemental analysis: found % C 61.20, % H 7.84, % S 9.62, % Na 6.88 calcd % C 61.23, % H 7.86, % S 9.62, % Na 6.90

Disulfonated meso-isomer:

$C^{13}$ NMR (DMSO): δ145.96 (2C), 144.84 (2C), 127.29 (2C), 125.55 (2C), 50.97 (2C), 33.87, 31.20, 28.83, 28.56, 26.87 (16C), 22.01 (2C), 13.67 (2C).

Elemental analysis: found % C 61.21, % H 7.84, % S 9.61, % Na 6.88 calcd % C 61.23, % H 7.86, % S9.62, % Na 6.90.

Characteristic antisymmetric and symmetric $S=O_2$ stretching absorption for both surfactant isomers at ⁻1335 $cm^{-1}$ and 1150 $cm^{-1}$ respectively were observed from infrared (KBr) absorption spectra.

The surfactant character of the dl-diastereomeric pair and the meso isomer was established using the standard static tensiometric technique and measuring the decrease in air-water surface tension as a function of surfactant concentration. The surface tension vs. the natural log, 1n, of the concentrate profile for both isomers in 0.1N NaCl solution at 25° C. is shown in the Figure. The surface tension vs. 1n (concentration) profiles recorded are typical for a surfactant, thus confirming the surfactant character of the synthesized molecules.

EXAMPLE 2

This example details the synthesis and properties of a two tail-one head surfactant of the invention wherein $R1=R2=n-C_8H_{17}$, $R3=H$ and $R4=SOy-M+$, $M=Na$ and $y=3$. The surfactant was synthesized using the procedure of Example 1 with the following changes: a) The dialkyl isomers of trans-stilbene were not separated after alkylation; b) sulfonation of the dialkyl derivative was carried out with chlorosulfonic acid at a 1:1 mole ratio.

Elemental analysis found: % C 63.93, % H 8.18, % S 6.41, % Na 4.74 calcd % C 70.80, % H 8.92, % S 6.31, % Na 4.52 $C^{13}$ NMR (DMSO): δ146.41 (2C alpha to the benzene ring)

The surfactant of Example 2 is oil soluble. A 1% solution in hexadecane was easily prepared and solubility was confirmed by UV absorption spectroscopy. Additionally, a water-in-oil emulsion with 1 wt % surfactant, 89 wt % hexadecane and 10 wt % water was prepared.

What is claimed is:

1. A compound having the general formula

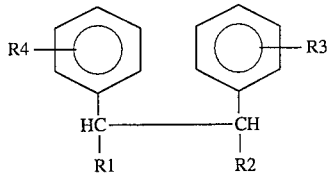

wherein R1 and R2 may be the same or different linear or branched hydrocarbon chains with carbon numbers 8 to 22; R3 is H, $SO_y^-M^+$, or $-O(CH2CH2O)_nX$; R4 is $SO_y^-M^+$, or $-O(CH2CH2O)_nX$; M is H, Li, Na, K, Rb or Cs; n is an integer from 2 to 50; y is 3 or 4; and, X is H or $SO_y^-M^+$.

2. The compound of claim 1 wherein R3=R4 when R3 is other than H.

3. The compound of claim 2 wherein R3 and R4 are at para positions.

4. The compound of claim 3 wherein M is Na or K.

5. The compound of claim 1 wherein $R_1$ and R2 are the same.

6. The compound of claim 5 wherein $R_3$ is other than hydrogen and R4=R3.

7. The compound of claim 6 wherein $R_3$ and $R_4$ are at para positions.

8. The compound of claim 7 wherein $R_3$ is $SO_yM^+$.

9. The compound of claim 7 wherein $R_3$ is $-O(CH2CH2O)_nX$.

* * * * *